United States Patent [19]

Matkovich et al.

[11] Patent Number: 5,472,621
[45] Date of Patent: Dec. 5, 1995

[54] METHOD FOR TREATING TRANSITION ZONE MATERIAL

[75] Inventors: Vlado I. Matkovich, Glen Cove; Thomas J. Bormann, Melville; Thomas C. Gsell; Frank R. Pascale, both of Glen Cove, all of N.Y.; Keith S. Morris, Hants, England

[73] Assignee: Pall Corporation, East Hills, N.Y.

[21] Appl. No.: 9,867

[22] Filed: Jan. 27, 1993

Related U.S. Application Data

[63] Continuation-in-part of Ser. No. 896,580, Jun. 10, 1992, abandoned.

[51] Int. Cl.⁶ ............................. B01D 37/00; B01D 21/26
[52] U.S. Cl. ........................ 210/767; 210/782; 210/787; 210/789; 210/806; 604/4
[58] Field of Search .................. 210/257.1, 295, 210/435, 436, 472, 496, 767, 782, 787, 789, 806; 604/4, 5, 6, 406, 408, 410; 422/101; 55/410, 418, 421

[56] References Cited

U.S. PATENT DOCUMENTS

| | | | |
|---|---|---|---|
| 3,000,540 | 9/1961 | Wheeler | 141/309 |
| 3,911,918 | 10/1975 | Turner . | |
| 4,223,695 | 9/1980 | Muetterties | 137/173 |
| 4,416,772 | 11/1983 | Sato et al. | 210/137 |
| 4,507,119 | 3/1985 | Spencer | 604/280 |
| 4,608,178 | 8/1986 | Johansson et al. | 210/744 |
| 4,857,190 | 8/1989 | Wada et al. | 210/232 |
| 4,985,153 | 1/1991 | Kuroda et al. | 210/782 |
| 4,997,577 | 3/1991 | Stewart | 210/767 |
| 5,053,127 | 10/1991 | Schoendorfer et al. | 210/196 |
| 5,071,570 | 12/1991 | Shiraki et al. | 210/774 |
| 5,100,564 | 3/1992 | Pall et al. | 210/782 |
| 5,102,407 | 4/1992 | Carmen et al. | 604/410 |
| 5,126,054 | 6/1993 | Matkovich | 210/641 |
| 5,128,048 | 6/1992 | Stewart et al. | 210/749 |
| 5,152,905 | 10/1992 | Pall et al. | 210/767 |
| 5,180,504 | 1/1993 | Johnson et al. | 210/767 |
| 5,217,627 | 6/1993 | Pall et al. | 210/767 |

FOREIGN PATENT DOCUMENTS

| | | |
|---|---|---|
| 0446713 | 9/1991 | European Pat. Off. . |
| 0455215 | 11/1991 | European Pat. Off. . |
| WO9117809 | 11/1991 | WIPO . |

OTHER PUBLICATIONS

"Preparation of Leukocyte–Poor . . . from Buffy Coats", Pietersz, et al., Vox Sang., 53:208–213 (1987).
"Improvement of Blood . . . New Bag System", Kretschmer et al., Infusionstherapie, 15:232–239 (Jun. 1988).
"Platelet Concentrates Stored . . . Glucose–Mannitol System", Pietersz et al., Vox Sang., 49:81–85 (1985).
Murphy, "Preparation and Storage of Platelet Concentrates", Principles of Transfusion Medicine, pp. 205–213 (1991).

*Primary Examiner*—John Kim
*Attorney, Agent, or Firm*—Leydig, Voit & Mayer

[57] ABSTRACT

Methods and devices for treating transition zone material are disclosed. Transition zone material is processed to form a supernatant layer which includes platelets and a sediment layer which includes red blood cells, and the supernatant layer is separated from the sediment layer by passing the supernatant layer through a porous medium. Once the supernatant layer has been separated from the sediment layer, gas may be separated from the supernatant layer.

15 Claims, 2 Drawing Sheets

5,472,621

METHOD FOR TREATING TRANSITION ZONE MATERIAL

This application is a continuation-in-part application of U.S. application Ser. No. 07/896,580, filed Jun. 10, 1992.

TECHNICAL FIELD

The present invention concerns a device and method for processing biological fluid.

BACKGROUND OF THE INVENTION

Blood consists of a number of components having different characteristics and uses. Advances in understanding these characteristics and uses have resulted in increased utilization of the specific fractions of blood, rather than whole blood, for therapeutic purposes. In view of the substantial therapeutic and monetary value of blood components, a variety of techniques have been developed to separate blood into its component fractions while ensuring maximum purity and recovery of each of the components.

The separation of a single unit of donated whole blood (generally about 450–500 milliliters in U.S. practice) into its components is typically accomplished by use of differential sedimentation. Typically, the principal components thus recovered are red cells, usually concentrated as packed red cells (PRC), platelet concentrate (PC), and plasma. The plasma may be further processed to yield a variety of valuable products.

There are two principal methods for separation of whole blood into components by differential sedimentation. In the most common method, the whole blood is typically centrifuged at a slow speed to produce a supernatant PRP fraction and a sediment PRC fraction, with a transition zone material in between, generally known as the buffy coat, which contains white blood cells (known collectively as leukocytes), as well as platelets, red cells, and plasma. The PRP fraction is separated from the buffy coat and PRC and then further processed by high speed centrifugation to produce a supernatant plasma fraction and a sediment platelet-containing fraction. The two fractions are then separated, and the platelet-containing fraction is processed to form PC.

In an alternative method, the whole blood may be centrifuged at a high speed to produce a supernatant platelet-poor plasma (PPP) fraction, and a sediment PRC fraction, with a transition zone material, the buffy coat, therebetween, which contains the majority of platelets, as well as leukocytes, red cells, and plasma. The buffy coat is separated from the supernatant PPP and the sediment PRC and then further processed by low speed centrifugation to form a supernatant platelet-containing fraction, and a sediment red cell containing fraction. The supernatant platelet-containing fraction is then separated from the sediment fraction, and processed to form PC.

However, despite the differences between the common and alternative methods, both techniques share several drawbacks, including the potential for red cell contamination and leukocyte contamination. With respect to red cell contamination, the presence of red cells in some blood components (e.g., PC) is so undesirable that the technician operating the blood processing equipment typically constantly monitors the process to ensure that red cells will be excluded. For example, regardless of whether the operator is separating PRP from PRC, or separating the buffy coat from the sediment PRC and/or separating the supernatant platelet-containing solution, the operator must closely monitor the separation and clamp the connecting tube between the blood bags when, in his judgment, as much fluid has been transferred as is possible, consistent with allowing no red cells to pass. This is a time consuming operation during which the operator must visually monitor the bag and judiciously ascertain when to shut-off the connecting tube.

The problem of red cell contamination presents an additional dilemma. Since platelets and plasma are valuable blood components, blood bank personnel may attempt to express more of the PRP or the supernatant platelet-containing fraction prior to stopping the flow from the blood bag. This is counterproductive in that the expressed fluid may be contaminated by red cells. The presence of red cells in PC is so highly undesirable that the PC may be discarded or subjected to recentrifugation, both of which increase operating costs and are labor intensive. As a result, blood bank personnel may err on the side of caution by prematurely stopping the flow of the platelet-containing fluid, e.g., PRP and/or supernatant platelet-containing fraction, before it has been fully expressed.

With respect to leukocyte contamination, both methods may produce leukocyte-containing fractions. It is now generally accepted that it is highly desirable to reduce the leukocyte concentration of each of the blood components by at least 70%, since the presence of leukocytes may adversely affect the storage life of the fractions, and/or cause undesirable effects when the fractions are transfused into a patient.

These problems may lead to reduced yields of valuable blood components since it may be difficult to eliminate red cell and leukocyte contamination while maximizing the yield of the various valuable blood components. For example, while the transition zone material or the buffy coat contains valuable platelets, plasma, and red blood cells, it may also contain a considerable amount of undesirable leukocytes. Since it may be difficult to easily or efficiently separate the various valuable components from each other, as well as from the leukocytes, the buffy coat may be partially or entirely discarded, resulting in reduced yields of valuable blood components such as plasma and platelets.

The loss of platelets is especially significant, since the lost platelets may include the most desirable platelets, i.e., the newly formed platelets. Newly formed platelets are larger and are generally believed to be more active. Since the younger platelets are larger, they tend to sediment faster during centrifugation, so these platelets may be concentrated as in one of the embodiments described below in the bottom of the PRP and in the buffy coat. Accordingly, since portions of these fractions or zone may be either processed as part of the PRC, or discarded, this represents a significant loss of the more desirable platelets.

For example, with respect to the conventional method of processing whole blood to form PRP and PRC, the buffy coat may be discarded after expression of the PRP and PRC layers, or, since the buffy coat may remain in the collection bag along with the PRC after the PRP fraction has been expressed, the buffy coat may be processed with the PRC.

Similarly, with respect to the alternative method of processing whole blood to form a buffy coat between PPP and PRC layers, and then processing the buffy coat to form a supernatant platelet-containing fraction and a sediment red cell containing fraction, the lower portion of the buffy coat may be processed with the PRC. For example, when the buffy coat is expressed before the PRC, the buffy coat may be incompletely expressed to prevent red cell contamination, and the lower portion of the buffy coat may be expressed with the PRC. Alternatively, when the PRC is expressed before the buffy coat, the lower portion of the buffy coat may be expressed along with the PRC.

Furthermore, in separating the supernatant platelet-containing fraction from the sediment red cell containing fraction, the lower portion of the supernatant platelet-containing fraction may be incompletely expressed to avoid red cell contamination, which may decrease the yield of the platelets.

Additionally, conventional methods for the processing of blood to provide blood components may lead to the presence of air, in particular oxygen, in the blood components or in the storage container. This may lead to an impairment of the quality of the blood components and may decrease their storage life. More particularly, oxygen may be associated with an increased metabolic rate (during glycolysis), which may lead to decreased storage life, and decreased viability of the blood components. Furthermore, the presence of air or gas in the satellite bag may present a risk factor to a patient's being transfused with a blood component. For example, as little as 5 ml may cause severe injury or death.

Accordingly, the previously described methods reflect a generally unsatisfying compromise between the pressing need to maximize the yield of the historically valuable blood components such as PC, plasma, and red cells from whole blood samples, and remove gas, while minimizing the effort and expense involved.

All of these problems are magnified when increased volumes (e.g., multiple units) of blood components are pooled or processed. Regardless of the particular method used to process blood into components, when multiple units of blood components are pooled before further processing, some of the fluid is trapped or retained in the individual collection and processing assemblies. Collectively, this represents a significant loss if the highly valuable fluid can not be recovered.

In view of this there is a growing need for a method and system for alleviating the above-described problems while providing maximum purity and a higher yield of superior quality blood components. In particular, there is a pressing need for a system and method for recovery and treatment of the transition zone material or the buffy coat which provides for a maximum yield and minimizes the presence of gas while delivering a greater proportion of viable and physiologically active platelets, e.g., by delivering a higher proportion of younger platelets.

There is also a pressing need for a method and system for efficiently pooling blood components, such as the transition zone material or the buffy coat, that maximizes the amount of fluid that can be recovered, while minimizing the presence of air.

Moreover, there is also a need for a method and system that is easily performed and provides for the separation of gas from the recovered fluid.

Definitions

In describing the present invention, the following terms are used as defined below.

(A) Biological Fluid: Biological fluid includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP), platelet-free plasma, platelet-poor plasma (PPP), plasma, packed red cells (PRC), transition zone material, buffy coat; analogous blood products derived from blood or a blood component or derived from bone marrow; red cell containing suspensions; and platelet-containing suspensions. The biological fluid may include leukocytes, or may be treated to remove leukocytes. As used herein, biological fluid refers to the components described above, and to similar blood products obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and donation to donation. Multiple units of some blood components, particularly platelets, and transition zone material or buffy coat, may be pooled or combined, typically by combining four or more units.

(B) Transition Zone Material or Buffy Coat: Transition zone material or buffy coat comprises a red cell-containing material spanning the interface between the supernatant cell-poor fraction and the sediment cell-rich fraction of separated biological fluid. As used herein, spanning the interface between supernatant and sediment layers encompasses a lower portion of the supernatant layer and an upper portion of the sediment layer as well as the material therebetween. Typically, the transition zone material or the buffy coat includes leukocytes. Preferably, the transition zone material or the buffy coat may include a high proportion of younger, more active platelets.

The transition zone material or the buffy coat may be formed by any method which separates components or fractions based on density and/or molecular weight, e.g., sedimentation, more preferably, centrifugation. The transition zone material or the buffy coat may be formed by soft-spin or hard-spin centrifugation. It is intended that the present invention is not to be limited by the process of forming the transition zone material or the buffy coat.

As used herein, a unit of transition zone material or buffy coat may be defined as the quantity derived from one unit of whole blood or derived from the biological fluid drawn during a single donation. Typically, the volume of a unit of transition zone material or buffy coat varies.

(C) Porous Medium: A porous medium is at least one porous structure through which a biological fluid passes. The porous medium for use with biological fluids may be formed from any natural or synthetic fiber or from a porous or permeable membrane (or from other materials of similar surface area and pore size or pore diameter) compatible with biological fluid (e.g., blood or a blood component). The surface of the fibers or membrane may be unmodified or may be modified to achieve a desired property. For example, the medium may be subjected to gas plasma treatment, an exemplary purpose for which may be to reduce platelet adhesion.

Although the porous medium may remain untreated, the fibers or membrane are preferably treated in order to reduce or eliminate platelet adherence to the medium. Any treatment which reduces or eliminates platelet adhesion is included within the scope of the present invention. For example, the fibers may be surface modified as disclosed in U.S. Pat. Nos. 4,880,548 and 5,100,564, in order to increase the critical wetting surface tension (CWST) of the fibers and to be less adherent of platelets. Defined in terms of CWST, a preferred range of CWST for a porous medium according to the invention is above about 70 dynes/cm, typically from about 70 dynes/cm to about 115 dynes/cm. A more preferred range is about 90 to about 100 dynes/cm and a still more preferred range is about 93 to about 97 dynes/cm.

The porous medium may be pre-formed, multi-layered, and/or may be treated to modify the fiber surfaces either before or after forming the fibrous lay-up. The porous medium may include at least one of a prefilter element or layer and a filter element or layer. The porous medium may additionally include at least one element or layer to provide support, better drainage, and/or improved flow characteristics, such as more uniform flow distribution. The porous medium may be configured in any suitable fashion, such as a flat sheet, a composite of two or more layers, a corrugated sheet, a web, a fibrous mat, a depth filter, or a membrane, although it is intended that the invention should not be limited thereby.

(D) Voids volume is the total volume of all of the pores within a porous medium. Voids volume is expressed hereinafter as a percentage of the apparent volume of the porous medium.

(E) Conversion of density when using fibers other than PBT: In the following exposition the term density is used, and the density values quoted for the porous medium are based on the use of PBT fibers. Other fibers which differ in density from the PBT may be used providing that their surfaces have, or have been modified to have, the characteristics noted above, e.g., a CWST of greater than 70 dynes/cm. In accordance with the invention, to use an alternate fiber of different density, the density of a porous medium made using an alternate fiber (i.e., the PBT equivalent density) may be calculated as follows:

Denoting V as a percentage of the voids volume relative to the apparent volume of the PBT medium [i.e., V=(volume of voids/volume of medium)×100], the objective is to calculate the density of an alternate fiber medium which will have a relative voids volume percentage equal to V.

If F is the density of the alternate fiber and 1.38 g/cc is taken as the density of PBT fiber, and $M_1$ is the density of the PBT medium and $M_2$ is the density required for a medium with equivalent performance, then voids volume V of the PBT fiber medium is $$V=(1-M_1/1.38)\times 100$$

and the density required for the medium made using the alternate fiber is $$M_2=F(1-V/100).$$

The more preferred fiber diameter range for the practice of this invention is about 2 to 3 μm, the diameter being defined in terms of surface area, as described in U.S. Pat. Nos. 4,880,548 and 5,100,564. This range is preferred because much above this range, the dimensions of the porous media and consequently the liquid hold-up volumes of the filter assemblies become significantly larger; below this range, the porous media become relatively less coherent and are more easily compressed. For example, a porous medium made using less than 2 μm polypropylene fibers would be compressed by the pressure developed by the plasma extractor, which can be as high as 300 mm of Hg.

Pore diameters of porous media in accordance with the invention can be determined using the modified OSU F2 method as described in U.S. Pat. No. 4,925,572. Filter assemblies with good efficiency and recovery can be made using large pore diameters, but such filter assemblies typically retain a higher proportion of platelets. A filter assembly having a pore diameter of about 15 μm to 30 μm or higher may allow some red cells and leukocytes to pass, thereby reducing platelet recovery efficiency. Therefore, it is preferred that the pore diameter not exceed 15 μm more preferably, less than about 10 μm. The most preferred pore diameter range is less than about 6 μm.

(F) In accordance with the invention, a useful technique for the measurement of fiber surface area, for example by nitrogen gas adsorption, is that developed by Brunauer, Emmet, and Teller in the 1930's, often referred to as the "BET" measurement. Using PBT as an example, the surface area of meltblown webs can be used to calculate average fiber diameter:

Total volume of fiber in 1 gram=$1/1.38$ cc
(where 1.38=fiber density of PBT, g/cc)
henc $$\frac{\pi d^2 L}{4} = \frac{1}{1.38} \tag{1}$$

Area of the fiber is $\pi dL = A_f$ (2)

Dividing (1) by (2)

$$\frac{d}{4} = \frac{1}{1.38 A_f} \text{ and } d = \frac{4}{1.38 A_f} = \frac{2.9}{A_f}, \text{ or } (0.345 A_f)^{-1}$$

where L=total length in cm of 1 gram of fiber,
d=average fiber diameter in centimeters, and
$A_f$=fiber surface area in cm²/g. If the units of d are micrometers, the units of $A_f$ become M²/g (square meters/gram), which will be used hereinafter. For fibers other than PBT, substitute the density for 1.38.

SUMMARY OF THE INVENTION

The present invention relates to processes and systems for treating a biological fluid to separate at least one fraction from the biological fluid and to remove gas from the separated fraction. Transition zone material or buffy coat may be processed to form a supernatant platelet-containing fraction and a sediment red cell-containing fraction, the platelet-containing fraction may separated from the red cell containing fraction, and gas may be separated from the platelet-containing fraction. The processes and systems of the instant invention may provide for the recovery of a greater proportion of young, viable, physiologically active platelets.

SPECIFIC DESCRIPTION OF THE INVENTION

Figure 1:
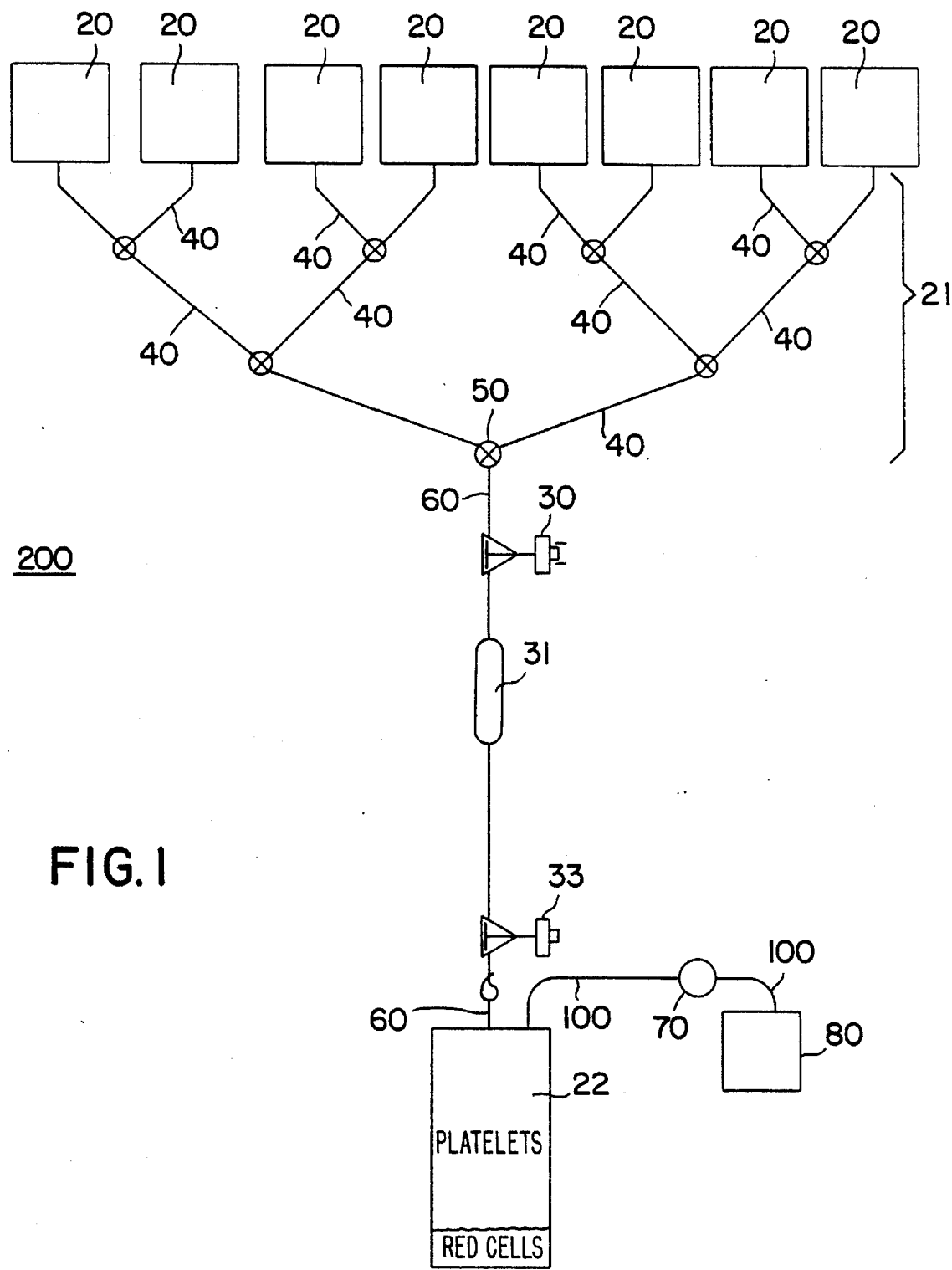
FIG. 1 is an embodiment of a biological fluid processing system comprising a manifold assembly according to the invention.

In accordance with the present invention, a method for treating a biological fluid comprises processing the transition zone material of a biological fluid to form a supernatant layer which includes platelets and a sediment layer which includes red cells, and separating the supernatant layer from the sediment layer by passing the supernatant layer through a porous medium, and separating gas from the separated supernatant layer by passing gas into a gas collection and displacement loop.

The present invention also provides a method for processing a biological fluid comprising processing a transition zone material of a biological fluid in a first container to form a supernatant layer which includes platelets and a sediment layer which includes red blood cells, separating the supernatant layer from the sediment layer by passing the supernatant layer through a porous medium and collecting the supernatant layer in a second container, and, separating gas from the supernatant layer by passing gas into a gas collection and displacement loop.

The present invention also provides a method for processing a transition zone material comprising pooling a transition zone material, processing the pooled transition zone material to form a supernatant layer which includes platelets and a sediment layer which includes red cells, separating the supernatant layer from the sediment layer by passing the supernatant layer through a porous medium until flow through the medium stops, and separating gas from the separated supernatant layer by passing the gas into a gas collection and displacement loop.

The present invention also provides a method for processing a transition zone material comprising passing transition zone material in a plurality of source containers through a pooling assembly to a receiving container, processing the pooled transition zone material to form a supernatant layer which includes platelets and a sediment layer which includes red cells, separating the supernatant layer from the sediment layer by passing the supernatant layer through a porous medium, and separating gas from the separated supernatant layer by passing the gas into a gas collection and displacement loop.

The present invention also provides a biological fluid processing assembly comprising a red cell barrier assembly including an upstream end and a downstream end, and a gas collection and displacement loop having a first end in fluid communication with the upstream end of the red cell barrier assembly and a second end in fluid communication with the downstream end of the red cell barrier assembly.

The present invention also provides a biological fluid processing system comprising a red cell barrier assembly including an upstream end and a downstream end, a gas collection and displacement loop having a first end in fluid communication with the upstream end of the red cell barrier assembly and a second end in fluid communication with the downstream end of the red cell barrier assembly, and, a container in fluid communication with the downstream end of the red cell barrier assembly.

Exemplary biological fluid processing systems, which are preferably closed, sterile systems, are shown in the Figures. As illustrated in FIG. 1, manifold assembly 200 may include containers 20, each suitable for holding at least one unit of a biological fluid such as transition zone material or buffy coat, in fluid communication with a pooling assembly 21. In the illustrated embodiment, the pooling assembly 21 includes a network or plurality of conduits 40 that converge into a single conduit 60 at outlet or junction 50. Some of the conduits 40 function as inlets to the pooling assembly 21 from the source containers 20. Alternatively, pooling assembly 21 may include a housing having at least two inlets and an outlet.

The outlet or junction 50 of the pooling assembly 21 is in fluid communication with a receiving or transfer container 22. In the illustrated embodiment, fluid communication with the receiving container 22 is preferably established by a conduit 60. Interposed in the conduit 60 between the outlet or junction 50 and the container 22 may be at least one device or assembly. For example, as shown in the illustrated embodiment, the manifold assembly 200 may include a gas inlet 30, a drip chamber 31, and a gas outlet 33.

The receiving or transfer container 22 may be in fluid communication with an additional or satellite container 80. In the embodiment illustrated in FIG. 1, fluid communication with the additional or satellite container 80 is preferably established by a conduit 100. Interposed between the receiving or transfer container 22 and the additional container 80 is a red cell barrier medium 70.

In another embodiment of a biological fluid processing system according to the invention, a container 90 may be in fluid communication with an additional or satellite container 80. In the embodiment illustrated in FIG. 2, fluid communication with the additional container is preferably established by a conduit 100. Interposed between the container 90 and the additional container 80 is a red cell barrier medium 70.

Figure 3:
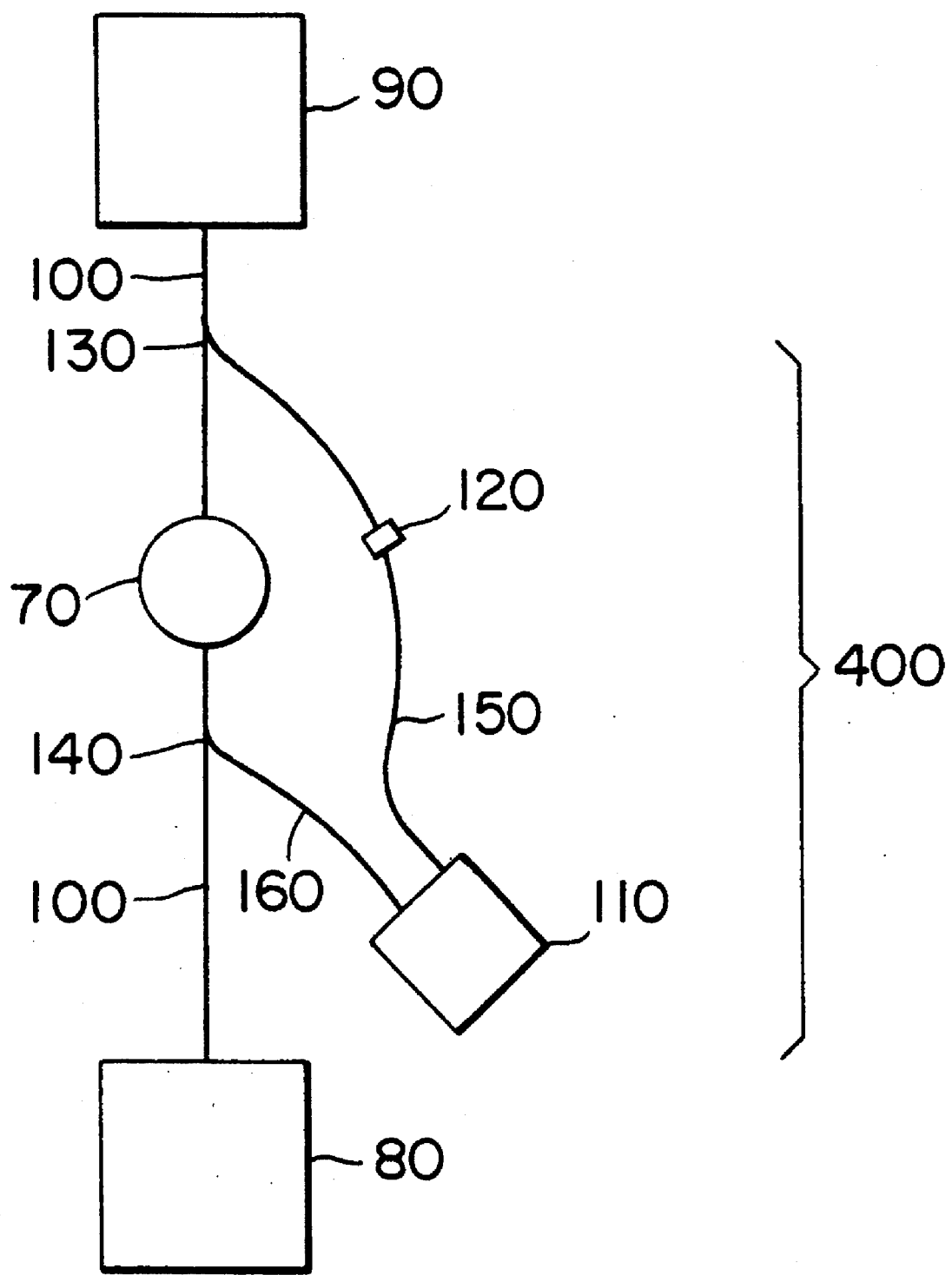
FIG. 3 is an embodiment of a biological fluid processing system including a gas collection and displacement lop according to the invention.

The invention includes a gas collection and displacement loop in FIG. 3 to separate gas from the biological fluid flow path. The gas collection and displacement loop 400, which includes a gas collection and displacement bag 110 interposed between the ends of a conduit, also includes a liquid barrier medium 120. Preferably, the liquid barrier medium is located within the conduit. The gas collection and displacement bag may be used to collect gas, and optionally, may be used for sampling a biological fluid.

The gas collection and displacement loop 400 may be in fluid communication with different components of the biological fluid processing system. Preferably, the ends of the gas collection and displacement loop are in fluid communication with the upstream and downstream, respectively, of a red cell barrier filter assembly. For example, one end of the gas collection and displacement loop may be connected via junction 130 to conduit 100 upstream of red cell barrier medium 70, and the other end of the loop may be connected via junction 140 to conduit 100 downstream of red cell barrier medium 70. Preferably, within the gas collection and displacement loop 400, the liquid barrier medium 120 is located closer to the connection, junction 130, to the conduit 100 upstream of the red cell barrier medium than is the gas collection and displacement bag 110.

The gas collection and displacement loop provides a safeguard that biological fluid contaminated with leukocytes will be isolated from leukocyte-depleted or processed biological fluid, since the contaminated fluid will not pass through the liquid barrier medium.

Each of the components of the invention will now be described in more detail below.

The containers which may be used in the biological fluid processing assembly may be constructed of any material and shape compatible with biological fluid and gas. A wide variety of these containers are already known in the art. For example, blood collection and satellite bags are typically made from plasticized PVC, e.g. PVC plasticized with dioctylphthalate, diethylhexylphthalate, or trioctyltrimellitate. The bags may also be formed from a polyolefin, polyurethane, polyester, or a polycarbonate.

As used herein, fluid communication may be established by any structure which allows the biological fluid and/or gas to pass from one location to another, such as by at least one conduit or tube. A flow control device such as a clamp, seal, valve, transfer leg closure, or the like, may be located within or on at least one of the conduits and/or the containers. The conduits used in the instant invention may be constructed of any material compatible with biological fluid and gas. Preferably, they may be composed of a flexible material, such as polyvinyl chloride (PVC), or plasticized PVC, e.g., PVC plasticized with dioctylphthalate, diethylhexylphthalate, or trioctyltrimellitate. There may be a number of conduits providing fluid communication to any individual container, and the conduits may be positioned in the system of the instant invention in a variety of ways. For example, there may be at least one conduit at the side, top, or bottom of the container, or combinations thereof. At least one conduit may extend within the interior of the container.

A red cell barrier medium, in accordance with the present invention, comprises a porous medium that separates a non-red cell containing biological fluid, such as a suspension of platelets and plasma, from a red cell containing biological fluid. The red cell barrier medium allows the non-red cell containing fluid to pass therethrough but stops the flow of the red cell containing fluid without allowing red cells to pass through the porous medium. Typically, the red cell barrier medium allows a platelet-containing fluid to pass therethrough, abruptly stopping flow when red blood cells block the medium.

A principal function of the red cell barrier medium is to separate a red cell containing fraction of a biological fluid from a non-red cell containing fraction. The red cell barrier medium may act as an automatic "valve" by stopping the flow of a red cell-containing biological fluid without allowing red cells to pass through the porous medium. The automatic valve function may quickly or instantly stop the flow of the red cell-containing biological fluid, thereby obviating the need for the operator to monitor this step.

The valve-like action is not well understood, but it is believed that flow is quickly or instantly stopped or inhibited due to aggregation in or on the medium of one or more constituents in the biological fluid. For example, at the present time, it is believed that as the non-red cell containing biological fluid passes through the medium, leukocytes are depleted from this fluid. These leukocytes appear to accumulate in or on the medium, but the remainder of the non-red cell containing fluid typically flows through the medium. However, once red cells directly or indirectly contact the medium, i.e., directly contact the medium or contact the leukocytes which, in turn, may directly contact the medium, flow through the medium ceases. Without intending to be limited to any particular explanation for the mechanism of this valve-like action, it is presently believed that the stoppage of flow may reflect aggregation of the red cells alone and/or in combination with leukocytes, forming a barrier which prevents or blocks further flow through the porous medium. It may be that other factors, such as the zeta potential, the CWST, and/or other characteristics of the fibers or the porous medium may contribute to the valve-like action.

This theory for the proposed mechanism is supported by the existence of filters capable of highly efficient leukocyte depletion of human red cell suspensions and which have pore sizes as small as 0.5 micrometers, through which red cells pass freely and completely with no clogging, with applied pressures of the same magnitude as that used in the present invention. On the other hand, the filters of the present invention, which typically have pore diameters larger than about 0.5 micrometers, abruptly stop the flow of red cells when the porous medium is contacted or penetrated by the red cells.

Exemplary red cell barrier media and red cell barrier/leukocyte depletion media are disclosed in U.S. Pat. Nos. 5,100,564; 5,152,905; and International Publication No. WO 91/04088.

A red cell barrier medium suitable for passing the platelets in about one unit of biological fluid preferably has a fiber surface area of about 0.04 to about $3.0M^2$, more preferably about 0.06 to about 2.0 $M^2$. A preferred range for the flow area is about 3 to about 8 $cm^2$, more preferably about 4 to about 6 $cm^2$. A preferred range for the relative voids volume is about 71% to about 83% (corresponding for PBT fibers to a density of about 0.23 to about 0.40 g/cc), more preferably about 73% to about 80% (about 0.27 to about 0.37 g/cc).

A red cell barrier/leukocyte depletion medium suitable for passing the platelets in about one unit of biological fluid preferably has a fiber surface area of from about 0.3 to about $2.0M^2$, more preferably from about 0.35 to about $0.6M^2$. A preferred range for the flow area is about 2.5 to about 10 $cm^2$, more preferably about 3 to about 6 $cm^2$. A preferred range for the relative voids volume is about 71% to about 83% (i.e., if PBT fiber is used, corresponding to a density of the medium in the range of about 0.23 to about 0.40 g/cc), more preferably about 75% to about 80% (for PBT, about 0.28 to about 0.35 g/cc). The upper limits of the flow area reflect the desire to accomplish the filtration in a relatively short period, and may be increased if longer filtration times are acceptable.

In accordance with the invention, the porous medium may be configured to remove a desired amount of leucocytes, preferably greater than about 70%, more preferably, in excess of about 99.9 to about 99.99%, which corresponds to an average residual leukocyte content per unit of less than about $0.005 \times 10^7$.

In other embodiments that may involve different volumes of biological fluid, e.g., pooled transition zone material, the red cell barrier and red cell barrier/leukocyte depletion media as disclosed above may be modified as necessary. Thus, the fiber surface area, flow area, density, and voids volume may be adjusted as necessary as is known to one of ordinary skill in the art. For example, the above listed ranges for the fiber surface area and flow area suitable for passing the platelets in about one unit of biological fluid may be multiplied by about six for passing the platelets from about six units of pooled transition zone material or buffy coat.

Although the red cell barrier medium of the present invention may have a substantially uniform density, another embodiment of the present invention may be of a construction such that an upstream portion of the medium is of generally lower density than a downstream portion. For example, the density of the red cell barrier medium may vary in a continuous or stepwise manner while maintaining an average density range suitable for separating a supernatant layer which includes platelets from a sediment layer which includes red cells. An exemplary red cell barrier medium may include a density range in the upstream portion from about 0.1 g/cc to about 0.23 g/cc, and a density range in the downstream portion from about 0.23 g/cc to about 0.40 g/cc. In another embodiment of the invention, the red cell barrier medium may include two or more layers, preferably of different or varying density. An exemplary zoned or layered fibrous medium using PBT as the fiber may include an upstream layer having a density range from about 0.1 g/cc to about 0.2 g/cc, a middle layer having a density range from about 0.20 g/cc to about 0.25 g/cc, and a downstream layer having a density range from about 0.23 g/cc to about 0.40 g/cc.

Included within the scope of the present invention are the use of other density values, in a particular zone or layer as well as throughout the red cell barrier medium. These alternative density ranges may be chosen based on achieving a desired result, in addition to separating a sediment layer from a supernatant layer, e.g., the flow rate, the type of fiber used, the amount of leukocytes removed, as well as other considerations.

Figure 2:
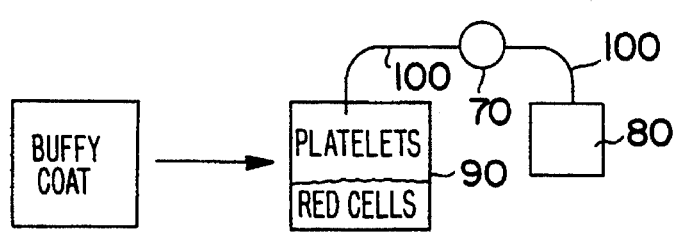
FIG. 2 is an embodiment of a biological fluid processing system according to the invention.

The red cell barrier medium may be positioned in the system of the instant invention in a variety of locations. For example, as illustrated in FIG. 2, it may be interposed between two containers, such as first container 90 and additional container 80. As illustrated in FIG. 1, it may be located downstream of the receiving or transfer container, for example, interposed between receiving or transfer container 22 and additional container 80, in conduit 100.

A leukocyte depletion medium which may be used in accordance with the present invention comprises a porous medium suitable for depleting leukocytes from the fluid passing through the leukocyte depletion medium. A leukocyte depletion medium suitable for passing the platelets in about one unit of biological fluid preferably has a fiber surface area of from about 0.08 to about $1.0M^2$, more preferably from about 0.1 to about $0.7M^2$. A preferred range for the relative voids volume is about 50% to about 89%, more preferably about 60% to about 85%. As described above with respect to the red cell barrier medium, these ranges may be adjusted as necessary as is known to one of ordinary skill in the art for those embodiments involving different volumes of biological fluid. For example, the above listed ranges for the fiber surface area may be multiplied by about six for passing the platelets from about six units of pooled transition zone material or buffy coat. Exemplary leukocyte depletion media are disclosed in U.S. Pat. Nos. 5,100,564 and 4,880,548 as well as International Publication No. WO 91/04088.

The leukocyte depletion medium may be positioned in the system of the instant invention in a variety of locations. Preferably, it is located downstream of the red cell barrier medium 70, i.e., interposed between the red cell barrier medium 70 and the additional container 80.

A porous medium may be used in a housing to form a filter assembly. Preferably, the porous medium is preformed to controlled dimensions and pore diameter prior to assembly in the housing to form an integral, self-contained element. Any housing of suitable shape to provide an inlet and an outlet may be employed. The housing may be fabricated from any suitably rigid, impervious material, including any impervious thermoplastic material, which is compatible with the fluid being processed. The housing may include an arrangement of one or more channels, grooves, conduits, passages, ribs, or the like, which may be serpentine, parallel, curved, circular, or a variety of other configurations.

Suitable exemplary housings are disclosed in U.S. Pat. Nos. 5,100,564, 4,923,620, 4,880,548 and 4,925,572, as well as International Publication No. WO 91/04088. It is intended that the present invention is not to be limited by the type, shape, or construction of the housing.

The gas collection and displacement loop 400 according to the invention includes a gas collection and displacement bag 100, a liquid barrier medium 120, and at least one conduit 160.

A gas collection and displacement bag 110 is a container suitable for collecting and storing gas. The gas collection and displacement bag may also be suitable for collecting and storing biological fluid. Suitable gas collection and displacement bags include the biological fluid processing containers as described previously. In a preferred embodiment it may be a flexible bag that may be squeezed so that gas in the bag can be passed to a desired destination.

The gas collection and displacement bag may also be used to increase the recovery of biological fluid. For example, after a platelet containing fluid passes from a receiving or transfer container 22 through at least one of a red cell barrier medium and a leukocyte depletion medium into a satellite container 80, the gas collection and displacement bag can be raised above the level of the satellite bag 80 to allow more platelet-containing fluid to drain into the satellite bag.

The gas collection and displacement loop 400 also includes a liquid barrier medium 120 through which gas passes but biological fluid will not. The liquid barrier medium may be any of a variety of means and devices which are capable of separating gas that may be present in the blood processing system from the biological fluid that is processed in the system.

A liquid barrier medium comprises at least one liquophobic porous medium. The liquid barrier medium may also include at least one liquophilic porous medium. Suitable liquophobic porous media and liquophilic porous media include, but are not limited to, those disclosed in International Publication No. WO 91/17809. The liquid barrier medium may be included in a housing. Suitable housings include, but are not limited to, those disclosed in International Publication No. WO 91/17809.

The conduits 150 and 160 in the gas collection and displacement loop may be as previously described. A flow control device such as a clamp, seal, valve, transfer leg closure, or the like, may be located within or one at least one of the conduits and/or the container.

The location of the liquid barrier medium may be optimized to achieve a desired result. Preferably, when the gas collection and displacement loop 400 is connected by a junction 130 and conduit 150 to conduit 100 upstream of red cell barrier medium 70, and by a junction 140 and conduit 160 to conduit 100 downstream of red cell barrier medium 70, the liquid barrier medium 120 is near to the junction 130 upstream of the red cell barrier medium 70.

The pooling assembly of the instant invention provides fluid communication between at least two source containers and a receiving container, preferably by channeling multiple flow paths into a single flow path. As illustrated in FIG. 1, the pooling assembly 21 preferably comprises a plurality of conduits 40 and an outlet or junction 50. Although the conduits can be configured in a number of ways, the pooling assembly preferably comprises a network or tiered arrangement of conduits 40, preferably including one or more junctions, such as one or more Y-connectors. As used herein, the conduits provide fluid communication between the source of the biological fluid, such as separate unit containers 20, and a multiple unit container, such as transfer or receiving container 22. A clamp, seal, valve, transfer leg closure, or the like, may be located within or on at least one of the conduits.

Alternatively, the pooling assembly 21 may include at least one device having multiple inlets and a single outlet in fluid communication with junction 50.

The pooling assembly used in the instant invention may be constructed of any material compatible with a biological fluid. For example, the pooling assembly may be composed of a non-flexible material, for example, acrylonitrile butadiene styrene (ABS), polycarbonate, or stainless steel. Alternatively, it may be composed of a flexible material, such as polyvinyl chloride (PVC), or plasticized PVC, e.g., PVC plasticized with dioctylphthalate, diethylhexylphthalate, or trioctyltrimellitate.

In accordance with another embodiment of the invention, the biological fluid processing system may include a drip chamber 31. The drip chamber 31 may be used to control flow rate and/or prevent gas from reaching a container such as a receiving or transfer container 22 downstream of the drip chamber, and for maximizing recovery of the biological fluid.

The drip chamber which may be used in the system may be constructed of any material compatible with biological fluid and gas. Furthermore, the drip chamber may include at least one porous element, preferably a liquophobic porous membrane, that allows gas into and/or out of the processing system, but resists or prevents the passage of biological fluid. The porous element may be positioned in a conduit, or more preferably, it may be included in the housing of the drip chamber. Further, the surface of the element may be oriented in a variety of ways with respect to the flow of the biological fluid. For example, two porous elements may be placed at opposite ends or sides of the drip chamber, or a single element may be within the drip chamber.

In another embodiment of the invention, a gas inlet and/or a gas outlet may be used to maximize the recovery of biological fluid in receiving or transfer container 22 and/or additional container 80. Exemplary gas inlets and gas outlets and processes for using them are as disclosed in International Publication No. WO 91/17809.

The gas inlet 30 and the gas outlet 33 may be, respectively, upstream and downstream of the drip chamber 31. More preferably, as exemplified in FIG. 1, the gas inlet 30 is downstream of the outlet of the pooling assembly 50 and upstream of the drip chamber 31, which is upstream of the gas outlet 33, and the gas outlet 33 is interposed between the drip chamber 31 and the receiving or transfer container 22. Alternatively, a gas inlet and/or a gas outlet may be positioned in a drip chamber, a conduit, or the receiving, source, and/or additional containers.

In another embodiments (not shown), the gas inlet 30 and the gas outlet 33 may be respectively located upstream and downstream of at least one of a leukocyte depletion assembly, a red cell barrier assembly and a red cell barrier/leukocyte depletion assembly.

The gas inlet and/or gas outlet may be positioned to achieve a desired result, e.g., recovery of valuable biological fluid and/or removal of gas, as is explained in more detail below.

The gas inlet is a porous element which allows gas into a biological fluid processing system. Thus, the gas inlet may provide for increasing the recovery of a valuable biological fluid (e.g., transition zone material) that may otherwise be retained in various components of the system during processing and would otherwise be lost.

The gas outlet is a porous element which allows gas that may be present in a biological fluid processing system out of the system and/or permits gas to be separated from the biological fluid being processed. Thus, the gas outlet may provide for minimizing the volume of gases that remain in, or in contact with, a biological fluid. The gas outlet may also function as a gas inlet.

The gas inlet and gas outlet are preferably chosen so that the sterility of the system is not compromised.

The gas inlet and gas outlet each comprise at least one porous element designed to allow gas to pass therethrough.

A variety of materials may be used, provided the requisite properties of the porous element are achieved. These properties include the necessary strength to handle the differential pressures encountered in use and the ability to provide the desired filtration capability while providing the desired permeability without the application of excessive pressure. The porous elements of the gas inlet and the gas outlet should also preferably have a pore diameter of about 0.2 micrometer or less to preclude bacteria entering the system. Exemplary gas inlets and gas outlets and processes for using them are as disclosed in International Publication No. WO 91/17809.

Preferably, the gas inlet and gas outlet include at least one liquophobic porous element. Because the liquophobic porous element is not wettable, or poorly wettable, by the biological fluid being processed in the system, gas in the system that contacts the liquophobic element will pass through it, while the biological fluid will not. The gas outlet may also include at least one liquophilic porous element, that allows gas to exit, but not enter, the system. In a preferred embodiment of the invention, the gas outlet includes both a liquophobic membrane and a liquophilic membrane. Additionally, the gas inlet and/or the gas outlet may be included in a housing, which may include a cap or closure.

As noted above, the placement of the gas inlet and/or the gas outlet may be optimized to achieve a desired result. For example, the gas inlet 30 may be located as far upstream of the manifold outlet or junction 50 as is practical in order to sufficiently maximize the recovery of transition zone material from the manifold assembly 200. Thus, gas inlets may be located in each of the source containers 20 of the transition zone material to be pooled. Alternatively, the gas inlet 30 may be placed in a conduit 40 or downstream of the outlet or junction 50 of the pooling assembly 21.

Also, it may be desirable to locate the gas outlet 33 in conduit 60 downstream of the outlet or junction 50 and as close to receiving or transfer container 22 as is possible in order to maximize the volume of gas that is removed from the manifold assembly 200. Alternatively, the gas outlet may be located in the receiving or transfer container 22 itself. The gas inlet or the gas outlet may be located in the drip chamber 31. In one embodiment of the invention, a gas inlet and/or a gas outlet may be interposed between the source containers 20 and the receiving container 22, for example, in conduit 60.

Included within the scope of the invention is the use of more than one gas inlet and/or gas outlet.

The processing of biological fluid in the context of the present invention may take place at any suitable time, preferably soon after donation. For example, when the biological fluid is donated whole blood, it is typically processed as soon as practicable in order to maximize the number of components derived and to maximize blood component viability and physiological activity. Early processing may more effectively reduce or eliminate contaminating factors, including, but not limited to, leukocytes and microaggregates. In accordance with the subject invention, the biological fluid may be processed within about twenty hours of collection from the donor. The subject invention may also include processing biological fluid in accordance with United States practice, wherein the initial processing of whole blood is generally within about 8 hours of collection from the donor.

Movement of the biological fluid through the system may be effected by maintaining a pressure differential between a container such as a collection bag, and the destination of the biological fluid (e.g., a container such as a satellite bag), to cause to fluid to flow in a desired direction. Exemplary means of establishing this pressure differential may be by gravity head, applying pressure to the collection bag (e.g., by hand or with a pressure cuff), or by placing the satellite bag in a chamber which establishes a pressure differential between the satellite bag and the collection bag (e.g., a vacuum chamber). Also included within the scope of the invention may be expressors which generate substantially equal pressure over the entire collection bag. It is intended that the present invention is not to be limited by the means of creating the pressure differential.

In general, a unit of biological fluid (e.g., donor's whole blood) may be received directly into a container such as a collection bag and processed. Processing may include forming supernatant and sediment layers of the biological fluid, typically by centrifugation, and forming a first supernatant layer and a first sediment layer, with a transition zone material spanning the interface between the supernatant and sediment layers. The transition zone material may be separated from the biological fluid and processed pooled or unpooled, typically by centrifugation, to form a second supernatant layer and a second supernatant layer. The second supernatant layer may be separated from the second sediment layer.

The processing steps and conditions may be adjusted as is known to one of ordinary skill in the art. For example, if the biological fluid is separated into supernatant and sediment layers by centrifugation, the centrifugation parameters may be optimized as is known to one of ordinary skill in the art. Typical hard-spin centrifugation may be about 3000×g to about 4800×g for about 5 to about 10 minutes. Typical soft-spin centrifugation may be about 280×g to about 1500×g for about 5 to about 15 minutes. It is intended that the present invention is not to be limited to the centrifugation parameters.

In a preferred embodiment, biological fluid may be centrifuged at an elevated G force (hard-spin centrifugation) to form the first supernatant and first sediment layers, as well as the transition zone material. For example, whole blood may be centrifuged at high speed to form PPP and red blood cell layers, with the buffy coat spanning the interface between those layers.

In another embodiment, biological fluid may be centrifuged at a decreased G force (soft-spin centrifugation) to form the first supernatant and first sediment layers, as well as the transition zone material. For example, whole blood may be centrifuged at a low speed to form PRP and red blood cell layers, with the buffy coat spanning the interface between those layers.

Once the first supernatant and sediment layers, and the transition zone material have been formed, the layers and/or the transition zone material may be separated from each other using a pressure differential to cause them to flow in a desired direction, e.g., from the collection container toward a satellite bag.

Selectively clamping the collection bag may increase the efficiency of separation. For example, the container may be clamped between the first supernatant layer (e.g., the PPP or the PRP) and the transition zone, and/or clamped between the first sediment layer (e.g., the red cell layer) and the transition zone, and the individual layer(s) and/or zone may flow toward separate satellite bags. A similar result may be achieved by selectively arranging the conduits with respect to the collection bag and its contents.

The conduits may be selectively clamped to prevent or allow flow into a satellite bag. For example, the operator may visually monitor the bag and stop the flow by clamping the conduit when he or she feels the individual layer or zone has been sufficiently expressed. Alternatively, a monitoring device, e.g., a sensor or photocell, may monitor the flow rate, pressure, and/or optical density of the fluid being expressed so that the flow may be stopped at the appropriate time. The means for establishing the pressure differential may be oriented to ensure that a desired volume of fluid is expressed. It is intended that the present invention is not to be limited to the manner of monitoring the flow.

The first supernatant and first sediment layer may both be expressed, leaving only the transition zone material in the container. In another embodiment, the transition zone material may be expressed to another container, preferably after expression of the first supernatant layer or the first sediment layer.

It is intended that the present invention is not to be limited to the manner or order of separation and/or expression of the layers and/or transition zone material.

Preferably, multiple units of biological fluid such as whole blood are processed in individual containers and the resultant units of transition zone material are combined, e.g., pooled in at least one container. The multiple units of transition zone material may be combined or pooled by any method that provides for combining at least two units of a biological fluid. For example, at least two containers, each including transition zone material, may be connected in series, e.g., vertically, so that transition zone material may be pooled in a downstream container, preferably the most downstream container. In another embodiment, the multiple units of transition zone material may be passed through a pooling assembly 21 to combine or pool the transition zone material in a single container, such as a receiving or transfer container 22.

For example, in one embodiment, as illustrated in FIG. 1, where the components of the system are shown in a preferred vertical arrangement, with the source containers 20 at the highest point, the buffy coat in a plurality of containers 20 passes through the conduits of the pooling assembly 21 through outlet or junction 50 to receiving or transfer container 22. As the buffy coat flows, it may contact at least one device, assembly, or porous element, e.g., a gas inlet 30, a drip chamber 31, or a gas outlet 33, for preventing gas from reaching the receiving container, and for maximizing the recovery of the buffy coat, which is interposed between the source containers 20 and the receiving or transfer container 22.

In order to maximize recovery of transition zone material, air or gas may be introduced into the source containers 20 through the gas inlet assembly 30 or the gas outlet assembly 33, preferably by using a syringe (not shown). As used herein, air or gas refers to any gaseous fluid, such as sterilized air, oxygen, carbon dioxide, and the like; it is intended that the invention not be limited to the type of gas used. While the introduced fluid is preferably ambient air or a sterile gas, some non-gaseous fluids may also be suitable. For example, fluid that is lighter than or immiscible with the biological fluid and is non-reactive with it is included within the scope of the present invention.

Introducing gas into the source containers 20 may be accomplished by opening a flow path from the gas inlet 30 or the gas outlet 33 to the appropriate source container 20, while closing the flow path to the receiving or transfer container 22. For example, the clamps on the conduits leading to the receiving or transfer container 22 and all but one container 20 may be closed, so that when gas is introduced into the system, gas in the conduit will enter the open container. In a preferred embodiment, the process includes introducing gas sequentially into the source containers 20. The flow path to each source container may be closed after gas has been introduced into that container.

The flow path from the gas inlet 30 or the gas outlet 33 may be closed. The flow path to the first source container 20 is then opened, and as the transition zone material passes from the first source container 20, and flows through the pooling assembly 21 toward receiving or transfer container 22, it displaces the gas that was ahead of the column of flowing transition zone material; this gas may be exhausted or removed from the system, or displaced to another portion of the system. The gas may be vented from the system through a porous element in the drip chamber or in the conduit, or through an open gas outlet 33. Once the gas has been exhausted from the system, the gas outlet may be inactivated to prevent gas from entering the system. For example, the gas outlet may be inactivated by manually closing the outlet, e.g., by capping or clamping. Preferably, the gas outlet includes a liquophobic element, and more preferably, both a liquophobic element and a liquophilic element, which inactivates the outlet automatically, upon wetting by the transition zone material.

Once the gas ahead of the column of transition zone material has been exhausted and the flow of transition zone material has stopped, clamps adjacent to the other source containers are opened, preferably, sequentially, so that transition zone material from the other containers 20 may pass through the pooling assembly 21 toward the receiving or transfer container 22. The clamp adjacent to the receiving or transfer container 22 is opened so that the transition zone material can flow into the container 22. Preferably, the clamp adjacent to the receiving or transfer container 22 is opened before the clamps adjacent to the other source containers are opened.

Initiating the flow of transition zone material from the other source containers also displaces gas ahead of the other units of transition zone material. Preferably, this gas may be collected in drip chamber 31 interposed between the outlet or junction 50 and the receiving or transfer container 22. Passing the transition zone material through a drip chamber 31 may include collecting gas and/or controlling the rate of flow of the transition zone material.

Typically, drip chamber 31 is inverted until the buffy coat fills the drip chamber, at which point the drip chamber is returned to its normal orientation, and the buffy coat flows toward the receiving or transfer container 22.

As the transition zone material passes through the system, the gas ahead of the transition zone material may be exhausted through the gas outlet 33 as described previously, and pooled transition zone material is then recovered in the receiving or transfer container 22. Alternatively, gas may enter the receiving or transfer container 22 and be separated from the transition zone material by using a gas collection and displacement loop as described below to displace the gas to another portion of the system.

In order to maximize recovery of transition zone material, gas may be introduced behind the transition zone material retained in the system. The gas that was initially introduced into the source containers 20 through either the gas inlet 30 or the gas outlet 33 will follow the transition zone material as it flows through the conduits. This increases the recovery of the transition zone material, since the gas following the transition zone material "chases" the fluid from the conduits. Furthermore, after the transition zone material has passed through the pooling assembly into the receiving or transfer container 22 and the source containers 20 have collapsed, gas may be introduced behind the retained transition zone material by opening gas inlet 30. Additional transition zone material may then be recovered in the receiving or transfer container 22.

Once recovery of the transition zone material has been completed, receiving or transfer container 22 may be sealed and separated from the system. Preferably, receiving or transfer container is heat sealed, although other methods of sealing are also suitable.

Fluid, such as plasma or a storage solution, may be added to the transition zone material in receiving or transfer container 22. The transition zone material may be further processed immediately, or after the transition zone material has been stored. Preferably, processing the transition zone includes forming supernatant and sediment layers, typically by centrifuging the transition zone material, and forming a second sediment layer and a second supernatant layer. Individual units of transition zone material, or transition zone material that has been pooled in a container by another method, may be similarly processed.

For example, in a preferred embodiment, processing pooled buffy coat or individual units of buffy coat may include forming supernatant and sediment layers by centrifugation as noted above. In a more preferred embodiment, the buffy coat may be centrifuged at low G force (Soft-spin centrifugation) to form a supernatant platelet-rich layer and a sediment red cell layer.

As described with reference to the Figures, processing the second supernatant layer, typically a platelet-containing layer, preferably a platelet-rich layer, may include passing the platelet-containing layer from the receiving or transfer container 22 (FIG. 1) or the container 90 (FIG. 2) through at least one porous medium comprising at least one of a red cell barrier medium, a red cell barrier/leukocyte depletion medium, and a leukocyte depletion medium (not shown). Preferably, processing the second supernatant layer includes separating the supernatant platelet-containing layer from the sediment red cell containing layer by passing the supernatant layer through a red cell barrier medium or a red cell barrier medium/leukocyte depletion medium until flow through the medium stops. In the embodiments illustrated in FIGS. 1—3, the platelet-rich fraction may be recovered in an additional container 80, such as a satellite bag.

In accordance with the invention, a gas collection and displacement loop 400 may be used to separate gas from the biological fluid. Preferably, gas may be separated from the biological fluid while maintaining a closed, sterile system.

For example, a platelet-containing fluid may be passed from a transfer or receiving container 22 through at least one of a red cell barrier medium, a red cell barrier/leukocyte depletion medium and a leukocyte depletion medium and collected into a satellite container 80 along with the gas displaced by the platelet-containing fluid. Gas may be separated from the platelet-containing fluid by expelling it from the satellite container 80 into a gas collection and displacement loop.

In another embodiment according to the invention, gas may be expelled and a desired amount of platelet-containing fluid for sampling may be collected in the gas collection and displacement loop.

Typically, the gas collection and displacement loop is connected to conduits upstream and downstream of a filter assembly, and the conduit downstream of the assembly is in fluid communication with a satellite container 80. A receiving or transfer container 22, which contains a platelet-containing layer, is in fluid communication with the conduit upstream of the filter assembly.

According to the invention, the platelet-containing layer may be passed through at least one of a red cell barrier assembly, a red cell barrier/leukocyte depletion assembly and a leukocyte depletion assembly into the satellite container 80. This will also displace gas into the satellite container.

If desired, the gas collection and displacement bag in the gas collection and displacement loop may be held above the level of the satellite bag 80 to drain the platelet-containing layer into the satellite bag 80. Once the fluid has been drained, the gas collection and displacement bag may be lowered.

The satellite bag 80 may be squeezed to expel gas into the gas collection and displacement bag (hereinafter the gas bag) of the gas collection and displacement loop. For example, satellite bag 80 may be squeezed to pass gas into the gas bag of the gas collection and displacement loop until the platelet-containing fluid reaches the gas bag. Once the gas has been expelled from the satellite bag 80, the flow path between the satellite bag 80 and the gas bag in the gas collection and displacement loop should be closed.

Optionally, it may be desirable to separate or isolate a platelet sample from the platelet-containing fluid in the satellite container 80. In this embodiment of the invention, gas may be expelled as described above, along with an amount of platelet-containing fluid, which may be collected in the gas bag of the gas collection and displacement loop.

After the desired amount of platelet-containing fluid for sampling has been collected in the gas bag, gas may be separated from the sample by squeezing the gas bag to pass gas into another portion of the system, e.g., through the liquid barrier medium of the gas collection and displacement loop into receiving or transfer container 22. In a preferred embodiment, the gas collection and displacement loop includes a flow control device located between the liquid barrier medium and the connection of the loop to the conduit upstream of the filter assembly. The flow control device may be manually (e.g., with a clamp) or automatically (e.g., with a check valve) controlled. The platelet-containing sample may be separated or isolated at any suitable time. For example, the sample may be separated prior to storage, or later, e.g., shortly before administration.

In another aspect, e.g., involving a leukocyte depletion assembly interposed between receiving or transfer container 22 and satellite bag 80, the gas displaced into receiving or transfer container 22 through gas collection and displacement loop 400 may then be passed into the conduit upstream of the filter assembly, which may displace or "chase" some of the platelet-containing fluid retained in the filter assembly and/or in the conduit downstream of the filter assembly. This displaced platelet-containing fluid may be recovered in satellite container 80 without collecting gas, since the filter assembly will not completely drain.

In other embodiments, the manifold assembly 200 may comprise all of the components shown in FIG. 1, except for either the gas inlet 30 or the gas outlet 33, and the manifold assembly 200 may include a gas collection and displacement loop (not shown), for example, in communication with conduit 60 downstream of junction or outlet 50 and upstream of receiving or transfer container 22. In these embodiments, gas may enter the receiving or transfer container, and the gas may be displaced from the receiving or transfer container and collected in the gas collection and displacement loop.

The instant invention may provide for a closed, sterile environment. Preferably, the recovered fraction or fractions should be viable and functional e.g., circulate normally in the patient's bloodstream after transfusion. Thus, once processing has been completed, the desired fraction or fractions of biological fluid may be recovered under conditions in which an appropriate storage environment is maintained, if desired.

EXAMPLES

Example 1

Six units of buffy coat were prepared and pooled by draining each unit into a bag of suitable size. The total volume of the pooled buffy coat was 345 ml.

The filter medium and housing (forming a filter assembly) were produced in accordance with U.S. Pat. No. 5,100,564 and International Publication No. WO 91/04088. The filter assembly included a preformed red cell barrier/leukocyte depletion medium having a CWST of 93–97 dynes/cm, a diameter of about 6.4 cm, a flow area of about 32 cm$^2$, a thickness of about 0.152 cm, and a density of about 0.31 gm/cc, produced from PBT fibers having diameters of about 2.1 micrometers. The inlet of the assembly was connected to the outlet of the transfer bag containing the pooled buffy coat, and the outlet of the assembly was connected to an empty satellite bag to form a system.

The system was centrifuged to form a sediment layer containing red cells and a supernatant layer of platelet-containing fluid.

The system was carefully placed in a conventional expressor without disturbing the settled layer of red cells, and the red cell barrier assembly was primed and the supernatant layer was expressed.

After six minutes had passed the red cell layer contacted the filter medium and flow had stopped. The resulting platelet-containing supernatant layer was found to be highly depleted of leukocytes, i.e., less than $6.9 \times 10^4$/unit, and rich in platelets, i.e., $3.2 \times 10^{11}$/unit.

Example 2

A pooling assembly used to perform this example may utilize six units of buffy coat in individual 60 ml single-unit containers, a 600 ml transfer container, and a 600 ml satellite container, set up in a manner that generally corresponds to that described for FIG. 1. The manifold assembly should be arranged generally vertically, with the pooling assembly and the conduit to the transfer container having a total length of about 24 inches.

The gas inlet and gas outlet in accordance with International Publication No. WO 91/17809, may be positioned as in FIG. 1.

The filter assembly may be as described in Example 1.

Clamps on the conduits adjacent to the six single-unit containers of buffy coat, as well as the clamp on the conduit between the transfer container and the gas outlet, should be closed.

The gas outlet should be capped and a 60 cc syringe may be used to introduce air through the gas inlet and into the source containers. The plunger of the syringe may be drawn back to the "60 cc" mark, and the gas inlet uncapped, and then the syringe may be connected to the gas inlet. The clamp to the first single-unit container, which contains a unit of buffy coat, should be opened, and the plunger of the syringe pushed forward about 5–10 cc, thus introducing air into the first single-unit container. The clamp to that first container should then be closed. The same procedure should be followed with respect to the remaining five single-unit containers.

The syringe should be removed, the gas inlet recapped, and the gas outlet uncapped. The clamp to the first container should be opened to allow the buffy coat to flow from the first container, and the drip chamber should be inverted and squeezed to fill the chamber with buffy coat. The drip chamber should be returned to its normal orientation, and the buffy coat should flow through the drip chamber toward the transfer container. Air should be exhausted through the opened gas outlet, until the buffy coat contacts the liquophobic membrane in the gas outlet.

At this point, flow should stop, and the clamp on the conduit leading to the transfer container should be opened, and buffy coat should flow into the transfer container.

The above process may be repeated for each of the remaining five containers. The flow will stop when the six containers of buffy coat have drained.

At this point, residual buffy coat should remain in the drip chamber, and the conduits downstream of the gas inlet. To recover some of the retained buffy coat, the gas inlet should be uncapped, and the buffy coat conduits will drain into the transfer container.

The tubing leading to the transfer container should be clamped and heat sealed, and the transfer container separated from the pooling assembly for further processing. The transfer container may be placed in a centrifuge bucket and processed to form a sediment fraction of red cells as well as a supernatant fraction containing platelets.

A filter assembly may be connected to a satellite bag, and a gas collection and displacement loop may connected upstream and downstream of the filter assembly. The gas collection and displacement loop may be connected using Y-connectors upstream and downstream of the filter assembly. The gas collection and displacement loop includes a 100 cc gas collection and displacement bag and a liquid barrier medium. The liquid barrier medium is located within the gas collection and displacement loop in a conduit between the Y-connector upstream of the filter assembly and the gas collection and displacement bag. The liquid barrier medium includes a liquophobic membrane produced in accordance with International Publication No. WO 91/17809.

There may be a clamp on the conduit between the upstream of the filter assembly and the connector (hereinafter clamp A), as well as a clamp on the conduit between the connector upstream of the filter assembly and the liquid barrier medium (hereinafter clamp B). There may also be a clamp on the conduit between the gas collection and displacement bag and the connector downstream of the filter assembly (hereinafter clamp C), as well as a clamp on the conduit between the downstream of the filter assembly and the satellite bag. This clamp (hereinafter clamp D) may be located downstream of the connector that connects the downstream of the filter assembly to the gas collection and displacement loop.

Clamps A, B, C and D may be closed, and the transfer container may be connected to the conduit upstream of the filter assembly. The filter assembly may be positioned vertically. Clamps A and D may be opened and the supernatant platelet-containing fluid should be expressed from the transfer container through the filter assembly into the satellite bag until the flow through the assembly automatically stops, separating the platelet containing fraction from the sediment red cell containing fraction. Clamp A should be closed.

The gas collection and displacement bag may be raised above the level of the transfer container and clamp C should be opened. Raising the gas collection bag may allow additional platelet-containing fluid in the conduit downstream of the filter assembly to drain into the satellite bag. Once the fluid has drained, clamp C may be closed and the gas collection and displacement bag may be lowered. Then the satellite bag should be compressed until gas collects toward the upper portion of the satellite bag. Clamp C should then be opened while continuing to compress the satellite bag to expel gas from the satellite bag into the gas collection and displacement bag. Once the gas has been expelled, clamp C should be closed.

The tubing from the outlet side of the filter assembly may then be clamped and heat sealed, and the platelet-containing bag may be removed.

It is expected that greater than 90% of the platelets will pass through the porous medium, and that greater than 99.9% of the leukocytes will be removed.

Example 3

An assembly including a transfer container containing six units of pooled buffy coat, a filter assembly, a gas collection and displacement loop (with a gas collection and displacement bag and a liquid barrier medium), and a satellite bag, may be as configured as in Example 2. Clamps A, B, C and D may be located as in that Example. The buffy coat may be centrifuged in the transfer container and the supernatant platelet-containing layer passed through the filter assembly, and the gas in the satellite bag may be expelled as described in Example 2. However, before expelling the gas from the satellite bag, the bag should be agitated to mix the platelets, and once the gas has been expelled from the satellite bag, the satellite bag is then compressed until platelets enter the gas collection and displacement bag. Once the gas collection and displacement bag contains an appropriate amount of platelets, the gas collection and displacement bag may be raised until the platelets drain back into the satellite bag. This transfer between the satellite bag and the gas collection and displacement bag may be repeated two more times. Then the satellite bag may be compressed to expel gas and a desired amount of platelets for sampling into the gas collection and displacement bag. Clamp D (downstream of the filter assembly), and clamp C (on the conduit between the gas collection and displacement bag and the satellite bag), may be closed.

The gas collection and displacement bag may be compressed until gas collects toward the upper portion of the bag, and clamp B, which is located on the gas collection and displacement loop on the conduit between the connector upstream of the filter assembly and the liquid barrier medium, may then be opened, and air from the gas collection and displacement bag may be expelled from the bag through the liquid barrier medium into the transfer container. Clamp B may then be closed, and the tubing from the outlet side of the filter assembly, as well as the conduit leading from the gas collection and displacement bag and the transfer container, may be clamped and heat sealed, and the satellite and gas collection and displacement bags, each containing platelets, may be removed. If desired, the platelet-containing fluid in the gas collection and displacement bag may be sampled without compromising the sterility of the platelet-containing fluid in the satellite bag.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for processing a biological fluid comprising:

processing a transition zone material of a biological fluid to form a supernatant layer which includes platelets and a sediment layer which includes red blood cells;

separating the supernatant layer from the sediment layer by passing the supernatant layer through a porous medium into a downstream container; and, separating gas from the supernatant layer in the downstream container by passing gas and a portion of the supernatant layer from the downstream container into a gas collection and displacement loop.

2. The method of claim 1 wherein passing gas and a portion of the supernatant layer into the gas collection and displacement loop includes passing the gas and the portion of the supernatant layer into a gas collection and displacement bag.

3. A method for processing a transition zone material comprising:

pooling the transition zone material;

processing the pooled transition zone material to form a supernatant layer which includes platelets and a sediment layer which includes red blood cells; and separating the supernatant layer from the sediment layer by passing the supernatant layer through a porous medium into a downstream container; and, separating gas from the supernatant layer in the downstream container by passing gas and a portion of the supernatant layer from the downstream container into a gas collection and displacement loop.

4. A method for processing a biological fluid comprising:

passing a biological fluid through a leukocyte depletion filter assembly and into a container downstream of the filter assembly, thereby displacing gas into the downstream container;

passing gas and a portion of the biological fluid from the container into a gas collection and displacement loop.

5. The method of claim 4 wherein passing gas into the gas collection and displacement loop includes passing gas and biological fluid into a gas collection and displacement bag, and then passing gas from the bag through a liquid barrier medium.

6. The method of claim 4 wherein passing a portion of the biological fluid into the gas collection and displacement loop includes passing a platelet-containing fluid into the gas collection and displacement loop.

7. A method for processing a biological fluid comprising:

passing a biological fluid through a leukocyte depletion filter assembly and into a container downstream of the filter assembly;

separating gas displaced by the biological fluid into the container by passing the gas from the container into a gas collection and displacement loop; and, passing a sample of the biological fluid from the container into the gas collection and displacement loop.

8. The method of claim 7 including passing the gas through a liquid barrier medium in the gas collection and displacement loop.

9. The method of claim 7 including passing the sample of biological fluid into a gas collection and displacement bag in the gas collection and displacement loop.

10. The method of claim 9 wherein passing a sample of the biological fluid into the gas collection and displacement bag includes passing a sample of a platelet-containing fluid into the gas collection and displacement bag.

11. The method of claim 7 wherein passing gas into the gas collection and displacement loop includes passing gas into the gas collection and displacement bag, and passing gas from the bag through the liquid barrier medium.

12. A method for isolating leukocyte-depleted biological fluid from leukocyte-containing biological fluid in a closed sterile system comprising:

passing a leukocyte-containing biological fluid through a leukocyte depletion filter assembly and into a container downstream of the filter assembly; and, passing gas and a portion of the leukocyte-depleted biological fluid from the downstream container into a gas collection and displacement loop including a liquid barrier medium that prevents the passage of leukocyte-containing biological fluid therethrough.

13. The method of claim 12 including passing gas through the liquid barrier medium.

14. The method of claim 12 wherein passing gas and the portion of the leukocyte-depleted biological fluid from the downstream container into a gas collection and displacement loop includes passing the gas and fluid into a gas collection and displacement bag.

15. The method of claim 14 further comprising passing gas from the gas collection and displacement bag through the liquid barrier medium.

* * * * *